United States Patent
Chung et al.

(10) Patent No.: US 7,919,318 B2
(45) Date of Patent: Apr. 5, 2011

(54) PROCESS FOR ISOLATING VASCULAR ENDOTHELIAL CELLS FROM EMBRYOID BODIES DIFFERENTIATED FROM EMBRYONC STEM CELLS

(75) Inventors: Hyung-Min Chung, Namyangju-si (KR); Sung-Hwan Moon, Seoul (KR); Ju-Mi Kim, Yongin-si (KR); Soo-Hong Lee, Seoul (KR)

(73) Assignees: Chabio & Diostech Co., Ltd., Yongin (KR); College of Medicine Pochon Cha University Industry-Academic Cooperation Foundation, Pochon-si (KR)

( * ) Notice: Subject to any disclaimer, the term of this patent is extended or adjusted under 35 U.S.C. 154(b) by 0 days.

(21) Appl. No.: 11/913,295

(22) PCT Filed: Jun. 13, 2007

(86) PCT No.: PCT/KR2007/002840
§ 371 (c)(1),
(2), (4) Date: Oct. 31, 2007

(87) PCT Pub. No.: WO2008/153231
PCT Pub. Date: Dec. 18, 2008

(65) Prior Publication Data
US 2010/0144032 A1 Jun. 10, 2010

(51) Int. Cl.
*C12N 5/02* (2006.01)
(52) U.S. Cl. .......................................... 435/381; 435/366
(58) Field of Classification Search .................. None
See application file for complete search history.

(56) References Cited

U.S. PATENT DOCUMENTS

| | | | |
|---|---|---|---|
| 2003/0175954 A1* | 9/2003 | Shamblott et al. | 435/366 |
| 2004/0096967 A1 | 5/2004 | Gryseels et al. | |
| 2006/0199263 A1 | 9/2006 | Auger et al. | |
| 2007/0192881 A1* | 8/2007 | Brinster et al. | 800/14 |

FOREIGN PATENT DOCUMENTS

KR 10-0744440 8/2007

OTHER PUBLICATIONS

Y. Kumashiro, et al. "Isolation of Hepatocyte-like Cells From Mouse Embryoid Body Cells," Transplantation Proceedings, vol. 37, pp. 299-300, 2005.
Thomson, James A., et al., "Embryonic Stem Cell Lines Derived from Human Blastocysts," Science, vol. 282, pp. 1145-1147, Nov. 6, 1998.
Levenberg, Shulamit, et al., "Endothelial Cells Derived From Human Embryonic Stem Cells," Proceedings of the National Academy of Sciences, pp. 4391-4396, Apr. 2, 2002.
Asikainen, Tiina M., et al., "Enhancement of Angiogenic Effectors Through Hypoxia-Inducible Factor in Preterm Primate Lung In Vivo," American Journal of Physiology—Lung, Cellular and Molecular Physiology vol. 291, pp. L588-595, May 5, 2006.
Zhang, Su-Chun, et al., "In Vitro Differentiation of Transplantable Neural Precursors from Human Embryonic Stem Cells," Nature Publishing Group, vol. 19, pp. 1129-1133, Dec. 2001.
Ahn, Seong Eun, et al., "Primary Bone-Derived Cells Induce Osteogenic Differentiation Without Exogenous Factors in Human Embryonic Stem Cells," Biochemical and Biophysical Research Communications 340 (2006), pp. 403-408, Dec. 15, 2005.
Kim, Jumi, et al., "Effective Isolation and Culture of Endothelial Cells in Embryoid Body Differentiated from Human Embryonic Stem Cells," Stem Cells and Development, vol. 16, pp. 269-280, Jan. 15, 2007.

* cited by examiner

*Primary Examiner* — James S Ketter
(74) *Attorney, Agent, or Firm* — Rothwell, Figg, Ernst & Manbeck, P.C.

(57) ABSTRACT

The present invention provides a process for isolating vascular endothelial cells from embryoid bodies differentiated from embryonic stem cells, which comprises: (a) treating embryoid bodies differentiated from embryonic stem cells with 0.005-0.015% trypsin and 0.05-0.15 mM ethylenediaminetetraacetate (EDTA) to obtain vascular endothelial cell clusters; and (b) treating the vascular endothelial cell clusters with 0.1-0.5% trypsin and 0.5-2 mM EDTA so as to separate the vascular endothelial cell clusters into single cells.

8 Claims, 4 Drawing Sheets

[Fig. 1]
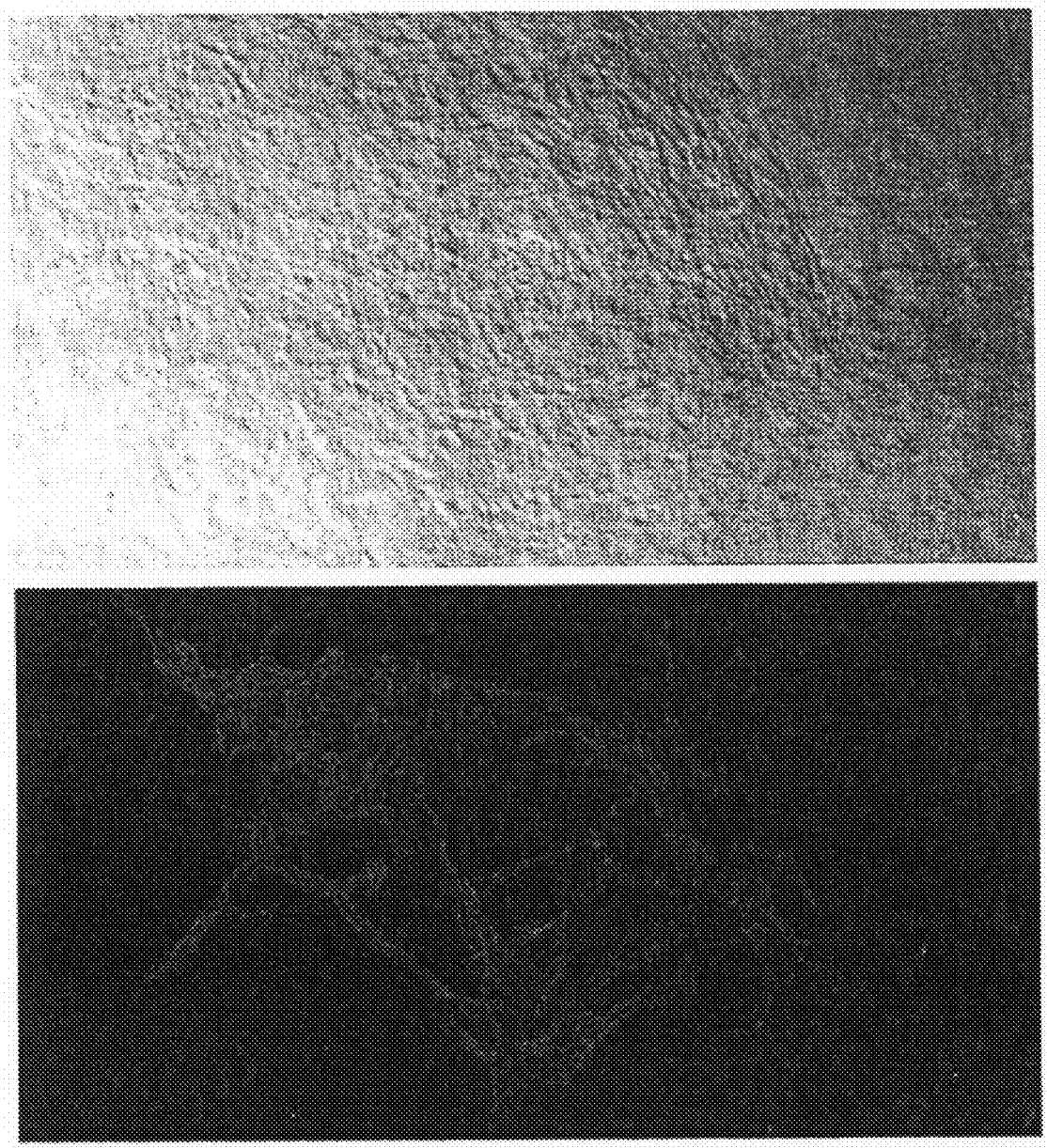
Lateral image

[Fig. 2]
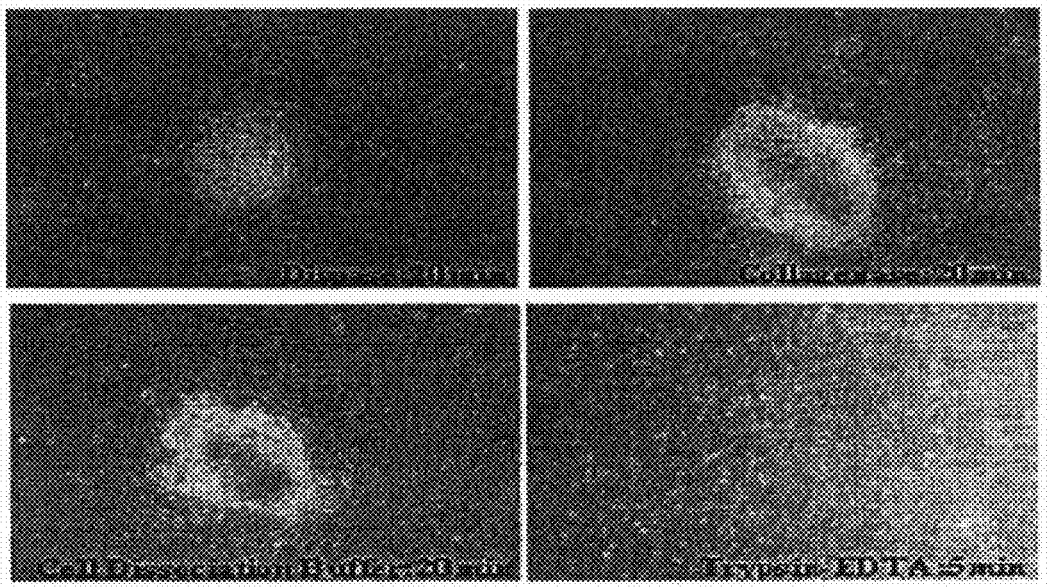
[Fig. 3]
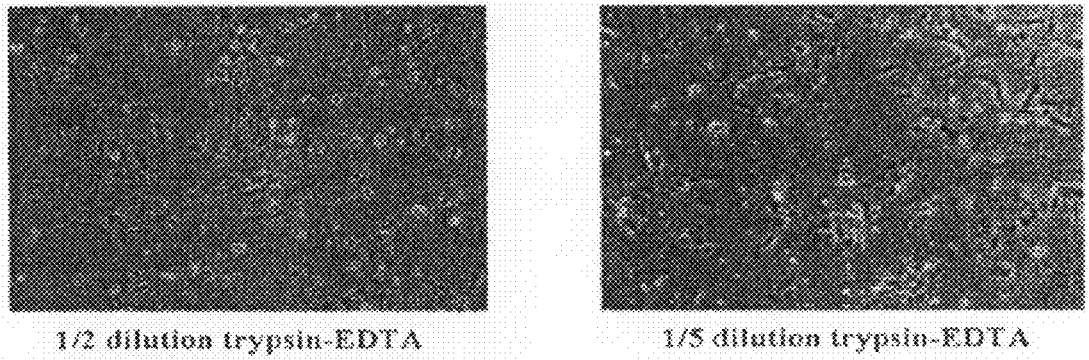
1/2 dilution trypsin-EDTA    1/5 dilution trypsin-EDTA
[Fig. 4]
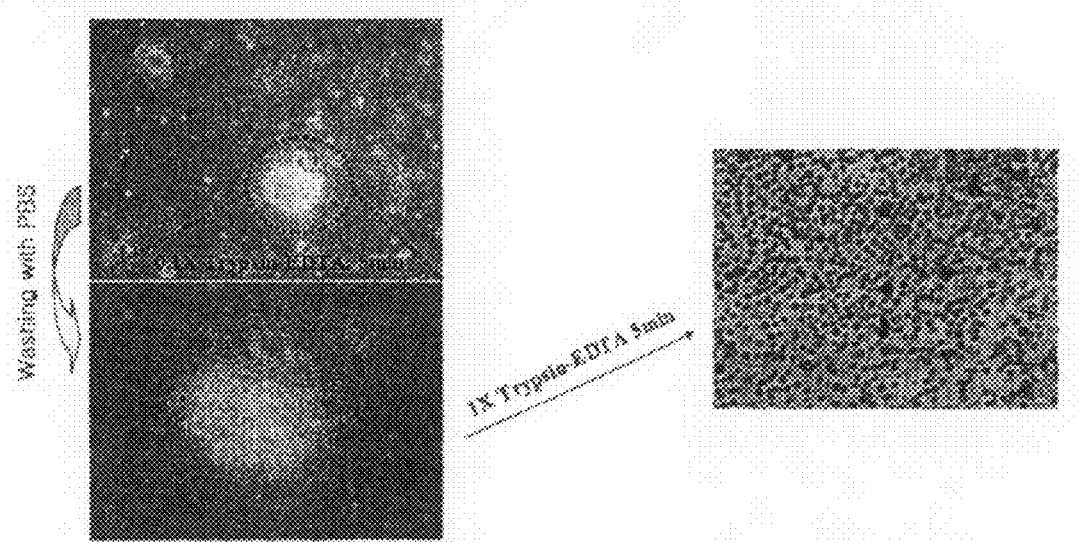

[Fig. 5]
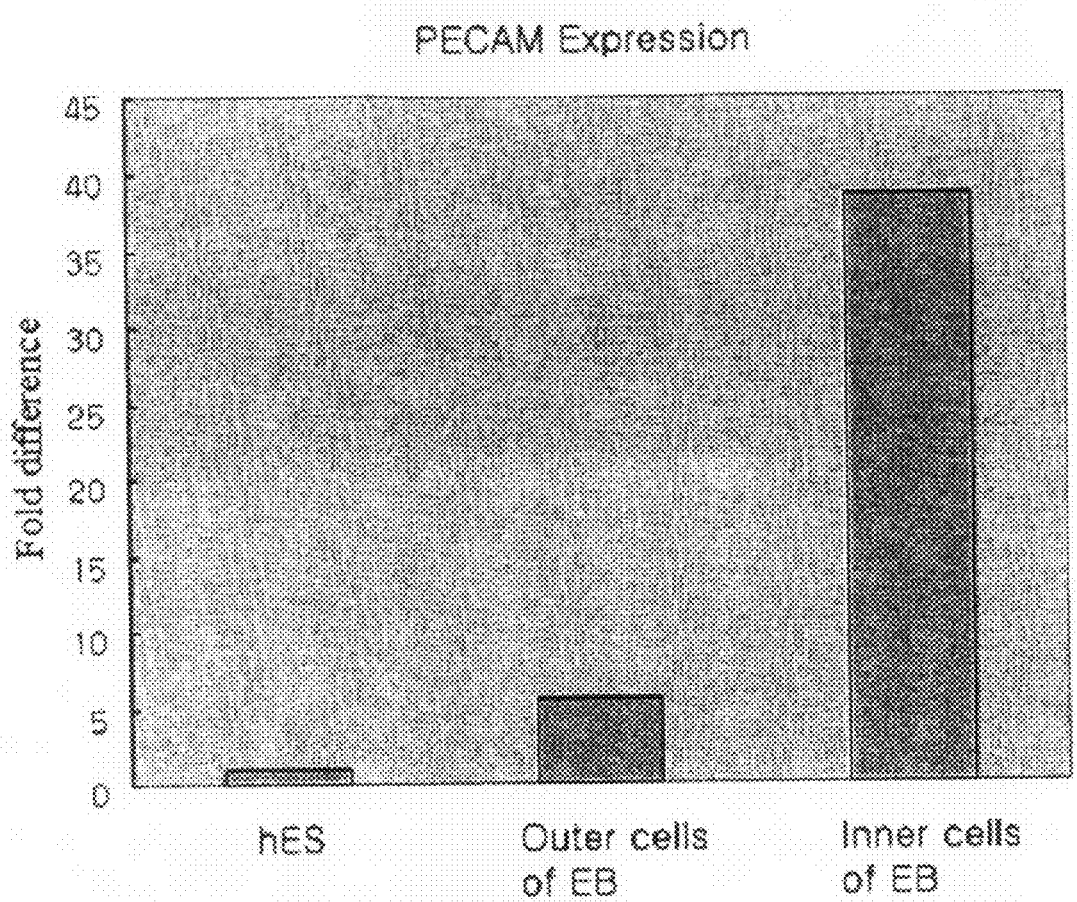
[Fig. 6]
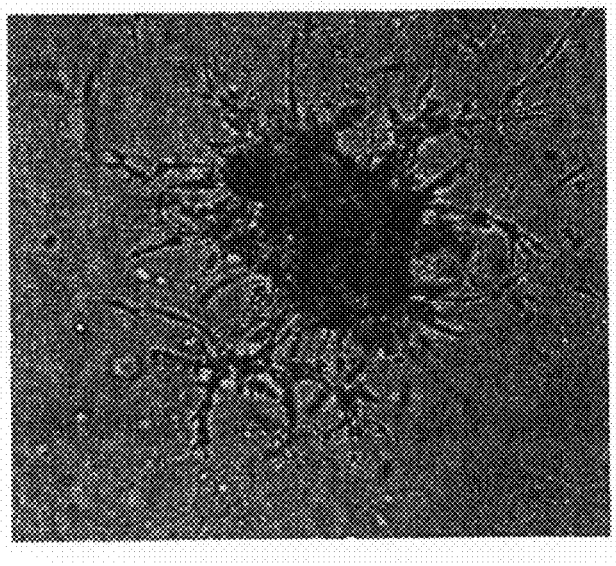

[Fig. 7]
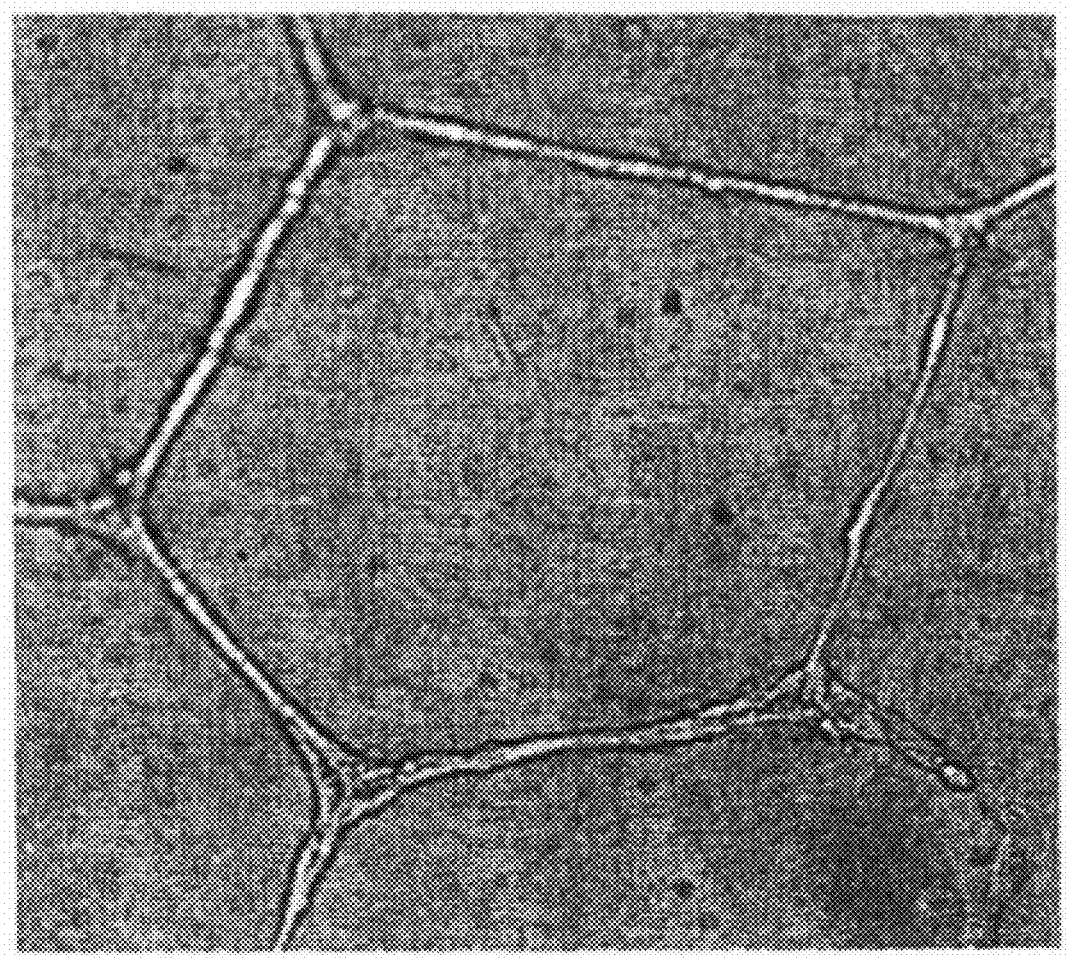

PROCESS FOR ISOLATING VASCULAR ENDOTHELIAL CELLS FROM EMBRYOID BODIES DIFFERENTIATED FROM EMBRYONC STEM CELLS

CROSS REFERENCE TO RELATED APPLICATIONS

This application is a 35 USC §371 National Phase Entry Application from PCT/KR2007/002840, filed Jun. 13, 2007, and designating the United States.

TECHNICAL FIELD

The present invention relates to a process for isolating vascular endothelial cells from embryoid bodies differentiated from embryonic stem cells.

BACKGROUND ART

Cardiovascular diseases are one of the leading causes of death worldwide. It is estimated that every year, about 12 million people throughout the world die due to cardiovascular diseases. Cardiovascular diseases are considered to be very serious diseases that cost the United States US$ 260 billion every year, but no effective treatment has yet been identified.

Recently, studies have been reported on inducing the differentiation of human embryonic stem cells into vascular endothelial cells, muscle cells, etc., raising hope for the possibility of treatment of cardiovascular diseases using human embryonic stem cells.

Human embryonic stem cells retain totipotency that is the ability to differentiate into three germ cell layers (endodermal, ectodermal, mesodermal) which organize the human body. Human embryonic stem cells can be differentiated into specific cells according to their surrounding environment, and thus, are expected to become potent tools that can achieve significant progress in the medical and science fields. Thus, it is expected that studies of human embryonic stem cells can provide important clues for primitive aspects of early stages of human differentiation and can play a critical role in studies of cell therapy for cardiovascular diseases and incurable diseases, such as Parkinson's disease, myocardial infarction, diabetes, and leukemia.

Human embryonic stem cells can be obtained by isolating and culturing the inner cell mass of an early-stage human embryo known as "blastocyst". Human embryonic stem cells retain totipotency, and at the same time, can be maintained in an undifferentiated state and can be continuously sub-cultured (Thomson J A, Itskovitz-Eldor J, Shapiro S S, Waknitz M A, Swiergiel J J, Marshall V S, Jones J M, Embryonic stem cell lines derived from human blastocysts. *Science* (1998) 282:1145-1147). Thus, if conditions for differentiation into specific cells, proliferation, isolation, and recovery are developed and established, cell therapy studies are expected to face a major turning point. In this regard, many studies about human embryonic stem cells have focused on establishing differentiation conditions that can induce the differentiation of human embryonic stem cells into specific cells, such as neural cells, vascular endothelial cells, cardiac cells, endothelial cells, and hepatocytes.

Differentiated embryoid bodies (EBs) include large amounts of other differentiated cell lineages and some undifferentiated cells, in addition to target cells. Thus, a technique of effectively isolating only target cells after differentiation is essentially required. However, satisfactory methods capable of selectively and efficiently isolating only target cells have not yet been reported.

Zhang S C et al. reported a method for isolating neural progenitor cells from differentiated embryoid bodies by dispase treatment (Zhang S C, Thomson J A et al. In vitro differentiation of transplantable neural precursors from human embryonic stem cells. *Nature Biotech* (2001) 19, 1129-1133). However, Zhang S C et al's report is related to isolation of neural progenitor cells and is silent about whether or not the isolation method can be applied to other types of differentiated cells, e.g., vascular endothelial cells.

In connection with differentiation and isolation of vascular endothelial cells from human embryonic stem cells, a method of differentiating human embryonic stem cells into embryoid bodies and isolating vascular endothelial cells from the embryoid bodies using a Fluorescence Activated Cell Sorter (FACS) has been reported (Levenberg S, Golub J S, Amit M, Itskovitz-Eldor J, Langer R. *PNAS* (2002) 99, 4391-4396). However, while isolating single cells from differentiated embryoid bodies using FACS, large amounts of the cells are destroyed, and further, the recovery rate of vascular endothelial cells is merely 2%.

DISCLOSURE OF THE INVENTION

Technical Problem

Therefore, in order to clinically apply differentiated vascular endothelial cells, a method for acquiring large amounts of healthy vascular endothelial cells with no contamination by other cells is required in the art.

Technical Solution

While searching for a high yield and selective method for isolating vascular endothelial cells differentiated from human embryonic stem cells, the present inventors have surprisingly found that when embryoid bodies differentiated from human embryonic stem cells are subjected to a two-step treatment of trypsin and ethylenediaminetetraacetate (EDTA) including a lower dose trypsin-EDTA treatment and a higher dose trypsin-EDTA treatment, specific regions of the embryoid bodies containing only a trace amount of vascular endothelial cells can be removed easily and rapidly, and the isolated vascular endothelial cells retain their intrinsic characteristics.

Therefore, the present invention provides a process for isolating vascular endothelial cells differentiated from embryonic stem cells.

BRIEF DESCRIPTION OF THE DRAWINGS

FIG. 1 is an image of embryoid bodies differentiated from human embryonic stem cells and an immunostained image showing the location of vascular endothelial cells in the embryoid bodies;

FIG. 2 is an image showing the degree of cell detachment from differentiated embryoid bodies according to the types of enzymes;

FIG. 3 is an image showing the degree of cell detachment from embryoid bodies according to the concentration of trypsin-EDTA;

FIG. 4 is optical microscopic images of vascular endothelial cells according to the treatment steps of trypsin and ethylenediaminetetraacetate (EDTA);

FIG. 5 shows RT-PCR results for undifferentiated human embryonic stem cells, outer cells of embryoid bodies, and vascular endothelial cells isolated according to the present invention; and FIGS. 6 and 7 are images obtained by culturing outer cells of embryoid bodies and vascular endothelial cells isolated according to the present invention, respectively, on Matrigels.

MODE FOR INVENTION

According to an aspect of the present invention, there is provided a process for isolating vascular endothelial cells from embryoid bodies differentiated from embryonic stem cells, which comprises: (a) treating embryoid bodies differentiated from embryonic stem cells with 0.005-0.015% trypsin and 0.05-0.15 mM ethylenediaminetetraacetate (EDTA) to obtain vascular endothelial cell clusters; and (b) treating the vascular endothelial cell clusters with 0.1-0.5% trypsin and 0.5-2 mM EDTA so as to separate the vascular endothelial cell clusters into single cells.

As used herein, the term "vascular endothelial cells" refers to cells which form an inner layer of a blood vessel and express markers such as PECAM, CD34, VE cadherin, eNOs, etc.

As used herein, the term "embryoid bodies" refers to aggregates composed of three germ cell layers (endodermal, ectodermal, mesodermal) differentiated from human embryonic stem cells. Embryoid bodies can be maintained in an appropriate medium.

The present inventors investigated the distribution of vascular endothelial cells in differentiated embryoid bodies using anti-PECAM antibodies, and as a result, found that most vascular endothelial cells are present in the center regions of embryoid bodies (see FIG. 1). According to the isolation method of the present invention, embryoid bodies are subjected to a two-step trypsin-EDTA treatment including a lower dose trypsin-EDTA treatment and a higher dose trypsin-EDTA treatment. When the embryoid bodies are treated with a lower dose trypsin-EDTA, the outer regions of the embryoid bodies containing only a trace amount of vascular endothelial cells are effectively removed and regions of the embryoid bodies containing large amounts of vascular endothelial cells are kept intact. When the embryoid bodies are treated with a higher dose EDTA-trypsin, vascular endothelial cell clusters are separated into single cells. As a result, vascular endothelial cells can be simply recovered in a high yield of about 30% or more.

The isolation method of the present invention includes forming embryoid bodies by culturing embryonic stem cells. The embryonic stem cells comprehend all embryonic stem cells derived from mammals. Preferably, the embryonic stem cells may be embryonic stem cells derived from human. The term "human embryonic stem cells" refers to totipotent cells derived from the inner cell mass of human morula. For example, the human embryonic stem cells may be, but not limited to, CHA-hES3 (Ahn S E, Kim S, Park K H, Moon S H, Lee H J, Kim G J, Lee Y J, Park K H, Cha K Y, Chung H M. Primary bone-derived cells induce osteogenic differentiation without exogenous factors in human embryonic stem cells. Biochem Biophys Res Commun. 2006 10; 340(2):403-408) or the like. In addition, the human embryonic stem cells can be easily established by those of ordinary skill in the art.

Formation of embryoid bodies from human embryonic stem cells can be performed by a method commonly known in the art. For example, according to the method disclosed in Levenberg S, Golub J S, Amit M, ltskovitz-Eldor J, Langer R. PNAS (2002) 99, 4391-4396, embryoid bodies can be formed by culturing human embryonic stem cells in a DMEM/F12 medium supplemented with serum (or serum replacement), L-glutamine, nonessential amino acid, and β-mercaptoethanol.

In the isolation method of the present invention, the embryoid bodies may be used in the form of a culture medium obtained by suspension-culturing them in an EB culture medium comprising serum replacement, mercaptoethanol, nonessential amino acid, and 80% KO-DMEM (KNOCK-OUT Dulbecco's modified Eagle's medium) for about 7-10 days. Preferably, the suspension-cultured embryoid bodies are cultured in a culture dish including a DMEM supplemented with fetal bovine serum (FBS), mercaptoethanol, and nonessential amino acid for about 24 hours so that attached embryoid bodies spread out.

In the isolation method of the present invention, trypsin may be a trypsin derived from a mammal (e.g., porcine trypsin) or a recombinant trypsin obtained by a recombination technique. EDTA used in the isolation method of the present invention may be in the form of ethylenediaminetetraacetic acid, ethylenediaminetetraacetate disodium, or ethylenediaminetetraacetate disodium dihydrate. Preferably, EDTA may be in the form of ethylenediaminetetraacetate disodium dihydrate.

Trypsin and EDTA may be used in the form of a solution in sterile physiological saline, preferably in an about 0.9% sodium chloride solution. Alternatively, a commercially available trypsin-EDTA solution (Sigma, U.S.A.) may be used in the form of a dilute solution containing desired concentrations of trypsin and EDTA.

In step (a), the concentration of trypsin is 0.005-0.015%, preferably about 0.01%, and the concentration of EDTA is 0.05-0.15 mM, preferably about 0.1 mM.

As described above, when embryoid bodies are treated with a lower dose trypsin-EDTA, the outer regions of the embryoid bodies containing only a trace amount of vascular endothelial cells are effectively removed, and regions of the embryoid bodies containing large amounts of vascular endothelial cells are kept intact. Trypsin and EDTA can be removed by washing with a physiologically compatible buffer, e.g., a phosphate buffered saline, or a medium.

In step (b), vascular endothelial cell clusters obtained in step (a), i.e., embryoid bodies containing large amounts of vascular endothelial cells are separated into single cells. Here, the concentration of trypsin is 0.1-0.5%, preferably about 0.25%, and the concentration of EDTA is 0.5-2 mM, preferably about 1 mM.

In steps (a) and (b), the trypsin-EDTA treatment may be performed for 3 to 10 minutes, preferably about 5 minutes.

As described above, when isolating vascular endothelial cells by a two-step trypsin-EDTA treatment including a lower dose trypsin-EDTA treatment and a higher dose trypsin-EDTA treatment, only regions of embryoid bodies containing a trace amount of vascular endothelial cells differentiated from human embryonic stem cells are selectively and simply removed, thereby minimizing cell damage, and thus, keeping the intrinsic characteristics of vascular endothelial cells intact. Therefore, obtained cells can maintain good blood vessel-forming capabilities.

Hereinafter, the present invention will be described more specifically with reference to the following examples. The following examples are only for illustrative purposes and are not intended to limit the scope of the invention.

Example 1

Mouse fibroblasts (STO cells, $2.5 \times 10^5$ cells/well), which had been treated with mitomycin-C for two hours to prevent cell proliferation, and feeder cell culture media (90% DMEM supplemented with 10% FBS, 0.1 mM mercaptoethanol, and 1% nonessential amino acid (Gibco)) were plated on gelatin-coated culture dishes, and the STO cells were cultured for 24 hours. The culture dishes were washed twice with phosphate is buffered saline media. The media in the culture dishes were replaced with culture media (80% KO-DMEM supplemented with 20% serum replacement (SR), 0.1 mM mercaptoethanol, 1% nonessential amino acid (Gibco), and 4 ng/ml bFGF), and human embryonic stem cells (CHA-hES3) were cultured for about seven days.

Human embryonic stem cell colonies formed in the culture media were detached from neighboring feeder cells by a glass pipette, and were then suspension-cultured in culture media including 20% serum replacement (Gibco), 0.1 mM mercaptoethanol, 1% nonessential amino acid (Gibco), and 80% KO-DMEM for about 10 days to form embryoid bodies. The suspension-cultured embryoid bodies were transferred to culture dishes including culture media (90% DMEM supplemented with 10% FBS, 0.1 mM mercaptoethanol, and 1% nonessential amino acid (Gibco)), and were then cultured for 24 hours so that the embryoid bodies spread out. Then, the media in the culture dishes were replaced with fresh media for about 10 days, every other day.

The distribution of vascular endothelial cells in differentiated embryoid bodies was investigated using anti-PECAM antibodies and the results are shown in FIG. 1. As shown in FIG. 1, most vascular endothelial cells are present in the center regions of embryoid bodies.

Example 2

Step 1: Lower Dose Trypsin-EDTA Treatment

The embryoid bodies obtained in Example 1 were seeded on culture media (90% DMEM supplemented with 10% FBS, 0.1 mM mercaptoethanol, and 1% nonessential amino acid (Gibco)). A 10-fold dilute solution of a trypsin-EDTA solution (Sigma, U.S.A.) of 0.25% trypsin and 1 mM EDTA in a 0.9% sodium chloride solution was added to the culture media, and the embryoid bodies were cultured for five minutes.

Step 2: Separation into Single Cells

The embryoid bodies obtained in step 1 were washed with a phosphate buffered saline to thereby completely remove cell clusters in the outer regions of the suspended embryoid bodies. A trypsin-EDTA solution (Sigma, U.S.A.) of 0.25% trypsin and 1 mM EDTA in a 0.9% sodium chloride solution was added, and the remaining cell clusters were cultured for five minutes to thereby separate the cell clusters into single cells.

Example 3

The same treatment as in Example 2 was performed except that in step 1, a 8-fold dilute solution of the trypsin-EDTA solution (Sigma, U.S.A.) was added to embryoid bodies, and the embryoid bodies were cultured for one, three, and five minutes.

Example 4

The same treatment as in Example 2 was performed except that in step 1, a 6-fold dilute solution of the trypsin-EDTA solution (Sigma, U.S.A.) was added to embryoid bodies, and the embryoid bodies were cultured for one, three, and five minutes.

Comparative Examples 1-3

The embryoid bodies obtained in Example 1 were seeded on culture media (90% DMEM supplemented with 10% FBS, 0.1 mM mercaptoethanol, and 1% nonessential amino acid (Gibco)). Then, dispase (Comparative Example 1), collagenase (Comparative Example 2), and a 1× cell dissociation buffer (Comparative Example 3) were added to the culture media, and the embryoid bodies were cultured for 20 minutes.

Comparative Examples 4-6

The same treatment as in Example 2 was performed except that in step 1, 5- and 2-fold dilute solutions of the trypsin-EDTA solution (Sigma, U.S.A.) (Comparative Examples 4 and 5, respectively), and the trypsin-EDTA solution (Sigma, U.S.A.) (Comparative Example 6) were added to embryoid bodies.

Experimental Example 1

The embryoid bodies obtained in Example 1 were treated with dispase, collagenase, a cell dissociation buffer, and trypsin-EDTA, like in Comparative Examples 1-3, and the degree of cell detachment from the embryoid bodies were measured using an optical microscope. The results are shown in FIG. 2.

As shown in FIG. 2, with respect to the embryoid bodies treated with the dispase, the collagenase, and the cell dissociation buffer, outer cell detachment from the embryoid bodies was not efficiently performed even when the embryoid bodies were cultured for 20 minutes. On the other hand, the embryoid bodies treated with trypsin-EDTA were separated into single cells in merely five minutes after the treatment.

Experimental Example 2

Based on the results of Experimental Example 1 demonstrating that trypsin-EDTA treatment is effective for cell detachment, the same treatment as in Comparative Examples 4-6 was performed in such a manner that step 1 was performed using a concentrated trypsin-EDTA solution and 5- and 2-fold dilute trypsin-EDTA solutions instead of the enzyme solution used in step 1 of Example 2, and the degree of cell detachment was measured using an optical microscope. The results are shown in FIG. 3. As shown in FIG. 3, no significant difference was found between the embryoid bodies treated with the trypsin-EDTA solution and the 5- and 2-fold dilute trypsin-EDTA solutions.

Experimental Example 3

RT-PCR was performed for the undifferentiated human embryonic stem cells used in Example 1, and the outer and inner cells of the embryoid bodies obtained in step 1 of Example 2, and PECAM specific to vascular endothelial cells was quantified. The results are shown in FIG. 4.

As can be seen from FIG. 4, when embryoid bodies are treated according to the present invention, outer cells of the embryoid bodies containing a trace amount of vascular endothelial cells can be effectively removed, and the embryoid bodies can be simply separated into single cells.

In addition, as a result of FACS (fluorescence activated cell sorter) analysis, the recovery rate of vascular endothelial cells was about 30% or more. The viability of the cells obtained in Example 2 was tested with trypan blue staining. As a result, it was determined that 95% or more of the cells were alive.

Experimental Example 4

RT-PCR was performed for the undifferentiated human embryonic stem cells used in Example 1, and the outer and inner cells of the embryoid bodies obtained in step 1 of Example 2, according to an Asikainen T M et al's method (Enhancement of angiogenic effectors through hypoxia-inducible factor in preterm primate lung in vivo. *Am J Physiol Lung Cell Mol Physiol.* 2006 May 5), and quantitative analysis for vascular endothelial cells was performed. The results are shown in FIG. 5. As can be seen from FIG. 5, when embryoid bodies are treated according to the present invention, the proportion of vascular endothelial cells among the inner cells of the embryoid bodies is about 7-fold or more higher than the proportion of vascular endothelial cells among the outer cells of the embryoid bodies.

Meanwhile, the outer cells of the embryoid bodies obtained in Example 1 and the single cells obtained in Example 2 were cultured on Matrigels, and the results are shown in FIGS. 6 and 7, respectively. As can be seen from FIGS. 6 and 7, cells isolated according to the present invention exhibit blood vessel-forming capabilities which are similar to those of vascular endothelial cells.

INDUSTRIAL APPLICABILITY

According to an isolation method of the present invention, among embryoid bodies differentiated from human embryonic stem cells, only regions of the embryonic bodies containing a trace amount of vascular endothelial cells are selectively and easily removed, thereby enabling rapid and efficient recovery of differentiated vascular endothelial cells. Due to the use of a low-concentration enzyme solution, cell damage is minimized, and thus, blood vessel-forming capabilities which are the intrinsic characteristics of vascular endothelial cells can be maintained at high level.

What is claimed is:

1. A process for isolating vascular endothelial cells from embryoid bodies differentiated from embryonic stem cells, which comprises:
   (a) treating embryoid bodies differentiated from embryonic stem cells with 0.005-0.015% trypsin and 0.05-0.15 mM ethylenediaminetetraacetate (EDTA) to obtain vascular endothelial cell clusters; and then
   (b) treating the vascular endothelial cell clusters with 0.1-0.5% trypsin and 0.5-2 mM EDTA so as to separate the vascular endothelial cell clusters into single cells.

2. The process of claim 1, wherein the embryonic stem cells are human embryonic stem cells.

3. The process of claim 1, wherein in step (a), the concentration of trypsin is 0.01% and the concentration of EDTA is 0.1 mM.

4. The process of claim 1, wherein in step (b), the concentration of trypsin is 0.25% and the concentration of EDTA is 1 mM.

5. The process of claim 1, wherein in steps (a) and (b), the treating with trypsin and EDTA is performed for 3 to 10 minutes, respectively.

6. The process of claim 2, wherein in step (a), the concentration of trypsin is 0.01% and the concentration of EDTA is 0.1 mM.

7. The process of claim 2, wherein in step (b), the concentration of trypsin is 0.25% and the concentration of EDTA is 1 mM.

8. A process for isolating vascular endothelial cells from embryoid bodies differentiated from embryonic stem cells, which comprises:
   (a) treating embryoid bodies differentiated from embryonic stem cells with 0.005-0.015% trypsin and 0.05-0.15 mM ethylenediaminetetraacetate (EDTA) to obtain vascular endothelial cell clusters; and
   (b) treating the vascular endothelial cell clusters with 0.1-0.5% trypsin and 0.5-2 mM EDTA so as to separate the vascular endothelial cell clusters into single cells;
   wherein the embryonic stem cells are human embryonic stem cells; and
   wherein in steps (a) and (b), trypsin and EDTA are treated for 3 to 10 minutes.

* * * * *